US006680039B2

(12) United States Patent
Hale, III et al.

(10) Patent No.: US 6,680,039 B2
(45) Date of Patent: Jan. 20, 2004

(54) SULFITE TREATMENT OF SPENT INDUSTRIAL WASTES

(76) Inventors: Edward Carroll Hale, III, 487 N. Walnut, Franklin, IN (US) 46131; John E. Wildey, 3240 Hickory Woods, Greenfield, IN (US) 46140

( * ) Notice: Subject to any disclaimer, the term of this patent is extended or adjusted under 35 U.S.C. 154(b) by 0 days.

(21) Appl. No.: 10/288,205

(22) Filed: Nov. 5, 2002

(65) Prior Publication Data

US 2003/0065238 A1 Apr. 3, 2003

Related U.S. Application Data

(63) Continuation of application No. 09/274,849, filed on Mar. 23, 1999, now Pat. No. 6,476,287.

(51) Int. Cl.[7] ........................ C01B 17/42; C07C 381/00

(52) U.S. Cl. ........................ 423/265; 423/519.2; 568/19

(58) Field of Search ................................ 106/407, 432, 106/819; 588/236, 257; 423/1, 23, 27, 45, 49, 52, 53, 57, 87, 99, 110, 111, 138, 153, 155, 178, 265, 519.2; 568/19

(56) References Cited

U.S. PATENT DOCUMENTS

| | | | | | |
|---|---|---|---|---|---|
| 2,154,996 | A | * | 4/1939 | Rawling | |
| 4,006,216 | A | * | 2/1977 | Ettel et al. | 423/592 |
| 4,130,440 | A | * | 12/1978 | Nose et al. | 106/74 |

* cited by examiner

*Primary Examiner*—Wayne A. Langel
(74) *Attorney, Agent, or Firm*—Woodard, Emhardt, Moriarty, McNett & Henry LLP

(57) ABSTRACT

A method of treating metal-contaminated spent foundry sand, or other industrial waste, by combining the sand with a sulfite to produce insoluble metal sulfur oxide complexes that do not leach from the sand. The treated waste may also be processed to reducing "clumping," thereby rendering the treated waste appropriate for use in another industrial process.

10 Claims, No Drawings

SULFITE TREATMENT OF SPENT INDUSTRIAL WASTES

CROSS REFERENCE TO RELATED APPLICATION

The present application is a continuation of U.S. patent application Ser. No. 09/274,849, filed Mar. 23, 1999, U.S. Pat. No. 6,476,287.

FIELD OF THE INVENTION

The present invention relates generally to methods of treating industrial waste, including spent foundry waste, and more particularly to a method of treating such waste to reduce the leachability of certain toxic metals and to process those wastes to make them suitable for use as a raw material.

BACKGROUND OF THE INVENTION

Industrial wastes, such as spent foundry sands and slags, typically contain leachable or extractable metallic contaminants. These wastes are then classified as hazardous or non-hazardous, or toxic/non-toxic, depending on the levels of contaminants indicated by various leach modeling methods, including: 1) Toxicity Characteristic Leaching Procedure (TCLP; EPA method 1311, "Test Methods for Evaluating Solid Waste, Physical/Chemical Methods" SW-846); 2) Synthetic Precipitation Leaching Procedure (SPLP; EPA Method 1312, "Test Methods for Evaluating Solid Waste, Physical/Chemical Methods" SW-846); 3) Multiple Extraction Procedure (MEP; EPA method 1320, "Test Methods for Evaluating Solid Waste, Physical/Chemical Methods" SW-846); and 4) Indiana Leaching Method, Neutral (Indiana NL; 329 Indiana Administrative Code 10-7-4(b)(3)(B)).

When the waste is hazardous or toxic, provisions exist for its disposal at a hazardous waste landfill. Because disposal in a hazardous waste landfill is expensive, hazardous or toxic waste is preferably treated to reduce the levels of contaminants to acceptable levels. The waste can then be disposed of at less expense in a non-hazardous waste landfill.

Although disposal of hazardous or toxic waste made non-hazardous or non-toxic by treatment is less costly than disposal of untreated toxic or hazardous waste, disposal of that waste is still relatively expensive. If the waste could be used in another industrial process, significant savings and environmental benefits could be achieved.

Some wastes have physical characteristics that enable them to be used in other industrial processes. For example, addition of pozzolanic coal ash to portland cement mixtures allows the derived concrete to obtain a much greater compressive and shear strength than concretes derived from portland cements alone. More specifically, addition of pozzolanic fly ash to portland cement is essential in obtaining compressive and shear strengths required for construction of certain articles. Furthermore, several states currently allow the use of foundry wastes as alternate raw materials.

However, many states require the levels of contaminants in foundry sands, slags and other industrial waste to be below certain levels prior to their reuse. Therefore, if they are present above those levels, the leachable and extractable metallic contaminants must first be chemically stabilized before the industrial waste can be utilized in another process.

Typical methods of treating industrial waste include adding to the waste either a phosphate compound in combination with a metal oxide and water or Portland cement (and/or cement kiln dust, quicklime, pozzolanic fly/bottom ash, etc.)

and water. These methods result in the waste becoming substantially solid and typically add at least ten percent by weight of other non-useful materials to the waste. Because of the need for subsequent crushing to form aggregate, these methods destroy the useful characteristics of wastes as substitute aggregate. For example, the particle size and shape distribution of foundry sands would be detrimentally altered after being treated by these methods. Moreover, although some prior art methods treat industrial waste with only a phosphate-containing compound, no steps are taken to retain or recover the particle size and shape distribution of the waste so it can be used in other industrial processes.

There is therefore a need for an economical method to treat industrial wastes such as foundry sands or slags. Specifically, there is a need for a method of treating industrial wastes that leave their useful particle shapes and size distributions unchanged so the wastes may be recycled as raw materials useful in other industrial processes.

SUMMARY OF THE INVENTION

Briefly describing one aspect of the present invention, there is provided a method of treating waste contaminated with leachable metallic contaminants by combining the waste with a sulfite such as calcium sulfite. The previously leachable metal contaminants are then complexed as insoluble metal sulfur oxides, and the material is safe for use as a raw material.

In another aspect of the invention, industrial wastes such as foundry sand or slag containing metallic contaminants is treated by first reducing the size of the sand or slag "clumps" or "chunks" until the sand or slag is returned to a particle size that is about the same as the size of the sand or slag particles before it was contaminated. The particles are then combined with a reactant effective for converting the metallic contaminants to a non-leachable form, and the product thus formed is useful as a substitute raw material in the production of, for example, concrete. In a preferred embodiment of this second aspect of the invention, the reactant is comprised of a sulfite such as calcium sulfite.

One object of the present invention is to provide a method for recycling industrial waste, including foundry sands and slags.

Further objects and advantages will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

The present invention relates to a method for reducing leachable levels of metallic contaminants such as antimony, arsenic, barium, beryllium, cadmium, chromium, lead, selenium, silver, nickel, iron, manganese, magnesium, aluminum, bismuth, copper, thallium, and zinc in industrial wastes, and particularly in foundry sands and crushed slags. In the most preferred embodiments the sizes and shapes of the sand or slag particles are returned to the size and shape distributions inherent to those materials before they became wastes. One advantage of the inventive method is that it provides treated wastes that are in a condition such that they are useable as raw materials in other industrial processes.

In one aspect of the present invention, the grain structure and size distribution of typical spent foundry sands are restored or retained to make that material useful as a fine aggregate when added to cement to form concrete. The grain structure allows the use of less portland cement in a concrete mix, while affording an equally strong or stronger end product. The cost reduction obtained by using less raw material, and the added strength imparted by the grain structure, are significant. Thus, foundry sands and crushed slags can be processed so as to make them eminently suitable for use as an aggregate, raw material, or fill material. Ready-mix concrete, brick and block, mortar, bricks, concrete blocks, etc., may all benefit from the inclusion of waste foundry sand that has been processed according to the present invention. Asphalt used in roadways, parking lots, etc., can benefit structurally from the inclusion of processed slag. Moreover, the inventive treatment may be utilized to make wastes more suitable for other uses where certain jurisdictions allow environmentally benign wastes to be used in manners other than as an industrial raw material.

In one aspect of the invention, the size of the waste is first reduced prior to being combined with a reactant. Slags are generally reduced in size for subsequent use as alternate raw material prior to application of the reactant. If the size of the slag is not reduced prior to treatment, only certain surfaces of the slag will be in contact with the reactant. This reduces the efficacy of the treatment, and reduces the chances that the slag will be accepted for beneficial use under applicable rules and laws. Slags tend to be glassy, and will shatter readily upon application of suitable forces such as those generated by aggregate crushers, hammer mills, or pug mills. This generates a range of particle sizes which must then be screened in order to separate out the most useful size distributions. Larger particles can be reprocessed until a suitable size is obtained.

Chemically bonded sands must be processed in such a fashion as to reduce the agglomeration back to its original size distribution, without damaging the beneficial aspect of the grain structure. The types of bonding agents added to the sands in preparation of cores or molds are engineered to be broken up into chunks by application of moderate force, such as is found on a typical shakeout table. Placing core pieces in a tumbling device similar to a concrete mixer, or a mill of some type will provide the necessary force to break down the agents bonding the sand grains together. When this processing step is performed in conjunction with addition of a chemical oxidizer such as hydrogen peroxide, the chemical bonding agents are further broken down prior to stabilization of the metallic contaminants. Heat is also effective in breaking down chemical bonding agents.

Sands containing a bentonite/coal dust (e.g., greensand) or other bonding agent which is used to form molds by compression do not require a particle size reduction step and are treated by addition of a reactant. However, as bentonite colors the greensand, the sand may require removal of the bonding agent by a washing step to meet the material specifications of the end user. For example, for a facility that prepares colored paver tiles or manufactures concrete products such as cisterns or septic tanks, the coloration imparted by the bond agent may be of no importance. If coloration is important, the washing step is easily accomplished by backflushing the sand with water. The washing step can occur prior to, or subsequent to, treatment. This process can be performed in a tank or other suitable apparatus.

After any required size reduction step, the sands or slags are treated with a reactant to render any toxic metal unleachable from the material. On one preferred embodiment the reactant is a phosphoric acid or phosphate oxide. In another preferred embodiment the reactant is an orthophosphoric acid or a polyphosphoric acid, including metaphosphoric acids, and their monosubstituted or polysubstituted salts such as sodium, ammonium or calcium phosphates (especially calcium phosphate in the triple-superphosphate form). The phosphate oxide is preferably phosphorus pentoxide. Furthermore, the phosphoric acid or phosphate oxide is preferably present in an aqueous solution.

In another embodiment of the invention, the reactant is typically comprised of organic or inorganic sulfides, sulfates, sulfites or bisulfites. Other agents that may be combined with the reactant include sulfuric acid, nitric acids, aluminum oxides, and oxides of tungsten such as tungstic acid.

Furthermore, heat or chemical oxidizers such as peroxides or permanganates may be used to remove organic bonding agents from chemically bonded sands. Moreover, certain agents may be added to adjust the final pH of the treated materials when pH considerations are necessary. For example, when the treated waste is to be used as a structural fill material, the treatment should be carried out at a substantially neutral pH as acidic or basic media may destroy clays and influence the transport of metals in groundwater or surface water systems. The pH-adjusting agents include, but are not limited to, the disubstituted or trisubstituted salts of phosphoric acid, such as disodium phosphate, diammonium phosphate and trisodium phosphate.

In the most preferred embodiment, the waste foundry sand is treated with calcium sulfite. For most foundry sands or slags, about 5% to 25% by weight dried calcium sulfite is sufficient to treat the waste material, although lesser or greater amounts may be required for a particular waste.

Treating the foundry sand with a reactant converts the metallic contaminants to a non-leachable form. For example, treatment of foundry sand or slag containing metallic contaminants with a phosphoric acid or phosphate oxide converts the metallic contaminants to an insoluble form in water or acid media. Treatment with a sulfite converts the metallic contaminants to an insoluble metal sulfur oxide complex, which does not leach from the treated material.

When phosphoric acid is used, the sands or slags are preferably sprayed with an aqueous solution of orthophosphoric acid. The solution must be of a suitable molarity and amount to completely coat the surface of all particles being treated, and to react with the leachable metallic contaminants present in the waste sands and additional materials. The solution strength and addition rate must be experimentally determined. The strength and quantity of the solution added will depend on the selection of reactant, the chemical makeup of the waste, waste porosity, the quantity of waste and the level of contaminants in the waste. The concentration and quantity of solution added can be determined by one of skill in the art by performing one or more of the appropriate leaching tests described above. Typically, an aqueous orthophosphoric acid solution comprising 0.1–5% phosphate by weight is used.

When calcium sulfite is used, the sulfite is first preferably dried before being combined with the waste material, although the sulfite may be added while wet. A small amount of thiosulfate or other sulfate inhibitor is preferably added with the sulfite to prevent formation of the sulfate.

Further as to the calcium sulfite embodiment, calcium sulfite is generated as a sludge in the exhaust gas desulfurization process stemming from use of coal as a fuel source. The exhaust gases are funneled through a slurry of calcium carbonate in water. Through a substitution reaction in an oxygen poor atmosphere, calcium sulfite is formed rather than calcium sulfate.

Atmospheric oxygen will naturally change the sulfite to sulfate, but addition of an oxidation inhibitor during the sludge generation process keeps this from happening. In the preferred embodiments, a small amount of thiosulfates are added as the inhibitor. In other embodiments, other oxidation inhibiting compounds may be used. Adding the inhibitor significantly improves performance however, because the sulfate form is not as useful in terms of reacting with metals to form insoluble metal sulfur oxide complexes.

The dewatered calcium sulfite sludge is then dried, and is ready to be added to a toxic waste and the mixture either disposed of or used as an alternate raw material. Drying is not essential to preparation of the treatment material, but it does facilitate handling and storage at the treating facility. If necessary, the wet sludge could be added to a waste, and the treatment would still be effected.

The sulfite embodiment proceeds by forming an insoluble metal sulfur oxide complex when soluble forms of toxic metals that are present in the waste go into solution. These insoluble complexes prevent leaching of the toxic metals from the waste.

Reference will now be made to a specific example using the processes described above. It is to be understood that the example is provided to more completely describe preferred embodiments and that no limitation to the scope of the invention is intended thereby.

EXAMPLE 1

Samples of foundry sand (greensand) that were classed as hazardous due to the presence of lead above the toxicity characteristic leaching procedure (TCLP) regulatory threshold set at 5 mg/L by the USEPA were obtained from a brass casting foundry. Ten percent by weight of dried calcium sulfite prepared by the aforementioned process was added to each of the samples and thoroughly mixed.

The waste/stabilized calcium sulfite mixture was subjected to the TCLP, and the leachate was tested for the presence of lead. The laboratory performing the analyses was capable of detecting and quantifying lead at levels of 0.5 mg/L in the leachate generated by the TCLP. In two of the samples, lead was not found at all. The third sample exhibited a lead level just above the detection limit (the sample result was 0.7 mg/L).

The data indicates that the addition of specially treated calcium sulfite to lead-bearing waste is efficacious in significantly reducing leachable levels of lead in wastes. After treatment, the waste was left with it's useful physical characteristics intact, and was suitable for use as an alternative raw material.

While the invention has been illustrated and described in detail in the foregoing description, the same is to be construed as illustrative and not restrictive in character, it being understood that only the preferred embodiment has been shown and described and that all changes and modifications that come within the spirit of the invention are desired to be protected.

What is claimed is:

1. A composition comprising a mixture of: (a) at least one metallic contaminant; and (b) a sulfite stabilized to prevent conversion of the sulfite to a sulfate; wherein said at least one metallic contaminant comprises lead.

2. The composition of claim 1 wherein said sulfite is calcium sulfite.

3. The composition of claim 1 wherein said sulfite is stabilized with a thiosulfate.

4. The composition of claim 1 wherein said sulfite is stabilized by formation of a sulfite ion donating mineral.

5. The composition of claim 1 where in said sulfite is an organic sulfite.

6. The composition of claim 1 wherein said sulfite is an inorganic sulfite.

7. The composition of claim 1 wherein stabilization of the oxidative state of the sulfite form occurs via mixing oxidation inhibiting compounds with sulfites, or synthesis and coprecipitation of oxidation inhibiting compounds during manufacture of the sulfite.

8. The composition of claim 1 wherein stabilization of the oxidative state of inorganic sulfites occurs via synthesis of a mineral, the structure of which inhibits oxidation of the sulfite to sulfate, while still acting as an effective sulfite ion donor.

9. The composition of claim 8 wherein stabilization of the oxidative state of the sulfite form occurs in a wet scrubber system via coprecipitation of hydrated calcium sulfite with small amounts of hydrated calcium sulfate, as a synthetic form of the mineral Hannebachite.

10. The composition of claim 1 wherein said "sulfite stabilized to prevent conversion of the sulfite to a sulfate" is calcium sulfite stabilized with a thiosulfate.

* * * * *